United States Patent [19]

Mukai et al.

[11] Patent Number: 5,767,091
[45] Date of Patent: Jun. 16, 1998

[54] ANALGESIC EFFECT ENHANCING PREPARATIONS

[75] Inventors: Kiyoshi Mukai; Hideaki Kohri, both of Tokushima, Japan

[73] Assignee: Otsuka Pharmaceutical Factory, Inc., Tokushima, Japan

[21] Appl. No.: 696,819

[22] PCT Filed: Feb. 7, 1995

[86] PCT No.: PCT/JP95/00155

§ 371 Date: Aug. 20, 1996

§ 102(e) Date: Aug. 20, 1996

[87] PCT Pub. No.: WO95/22967

PCT Pub. Date: Aug. 31, 1995

[30] Foreign Application Priority Data

Feb. 24, 1994 [JP] Japan ................... 6-026460

[51] Int. Cl.$^6$ .................. A61K 31/195; A61K 31/40; A61K 31/405; A61K 31/415
[52] U.S. Cl. .................. 514/23; 514/168; 514/365; 514/561; 514/562; 514/617; 514/643; 514/646; 424/601; 424/600; 424/678; 424/680
[58] Field of Search .................. 424/601, 600, 424/678, 680; 514/23, 168, 365, 561, 562, 617, 643, 646

[56] References Cited

U.S. PATENT DOCUMENTS 4,871,550 10/1989 Millman .................. 424/601

FOREIGN PATENT DOCUMENTS 0 424 028   4/1991   European Pat. Off. .
1-301619   12/1989   Japan .

*Primary Examiner*—Keith D. MacMillan
*Attorney, Agent, or Firm*—Sughrue, Mion, Zinn, Macpeak & Seas, PLLC

[57] ABSTRACT

The present invention provides an analgesic effect enhancing preparation capable of enhancement of the effect of analgesics, the preparation comprising as an active ingredient the following amino acid composition (%); leucine 8.0–16.0, isoleucine 4.0–9.0, valine 4.0–9.0, lysine 6.0–13.0, threonine 3.0–6.0, tryptophan 1.0–2.0, methionine 2.0–5.0, cysteine 0.5–2.0, phenylalanine 3.0–7.0, tyrosine 0.2–1.0, histidine 2.0–5.0, arginine 30.0–60.0, alanine 0.5–2.0, aminoacetic acid 0.5–2.0, serine 0.2–1.0, proline 0.5–2.0, aspartic acid 0.1–0.5 and glutamic acid 0.1–0.5, calculated as free amino acids.

The analgesic effect enhancing preparation of the present invention potentiates analgesic effect of various analgesics.

8 Claims, 2 Drawing Sheets

ANALGESIC EFFECT ENHANCING PREPARATIONS

TECHNICAL FIELD

The present invention relates to a preparation which enhances analgesic effect of analgesics. More specifically, the invention relates to a novel preparation capable of enhancing the effect of the analgesic when used in combination therewith to cancer patients or postoperative patients.

BACKGROUND ART

Heretofore there have been widely known and used various kinds of amino acid solutions supplied by means of parenteral alimentation to the patients such as cancer patients, postoperative patients and the like who are almost incapable of oral ingestion so as to achieve maintenance and improvement of the patients' physical fitness. Such known amino acid solutions are basically all alike in amino acid composition, simulating human milk, chicken eggs, human serum albumin, etc., and the composition is determined by consideration of oral alimentation to contain amino acid composition essential to the human body.

Cancer patients, postoperative patients and the like usually suffer from serious pain and these patients generally receive analgesics. However, the presently known analgesics induce side effects described below and have the problem of low effectiveness. Since cancer patients, postoperative patients and the like are in seriously bad physical conditions by invasion and even low in their drug metabolism, the analgesics are likely to produce side effects and ineffective for the treatment of chronic pain due to the development of tolerance.

Problems Associated With Analgesics (1) Narcotic and non-narcotic analgesics have problems of addiction and habituation.

(2) Several problems associated with antipyretic analgesics are reported, for example, kidney disorder caused by phenacetin, angiopathy caused by acetanilide, hepatopathy caused by aspirin, tissue disorder caused by intramuscular injection of sulpyrine, etc.

(3) Effective and safe drugs for treating chronic pain have not yet been developed due to the problem of tolerance.

Accordingly, it is an object of the present invention to provide a novel pharmaceutical preparation which can enhance analgesic effect of various kinds of analgesics when administered to cancer patients, postoperative patients and the like who receive analgesics, can control the development of tolerance associated with the repeated administration of analgesics and can reduce the side effect of analgesics, to thereby provide a highly safe total amino acid solution. It is also an object of the present invention to provide a novel pharmaceutical preparation which exerts equal or superior nutritive effect compared to the conventional nutritive amino acid solutions.

DISCLOSURE OF THE INVENTION

The inventors conducted extensive research to attain the above-mentioned objects and found that the amino acid solution which was proposed as amino acid preparation applied to cancer patients (see Japanese Examined Patent Publication No. 79049/1993) having a specified composition, in which branched amino acids and arginine are enriched, can not only exhibit excellent nutritive effect when administered to the cancer patients, postoperative patients and the like suffering from serious pain such as various central pain, cancerous pain, cluster headache, cervical syndrome or the like by supplying sufficient protein sources (amino acids), but also serve as an enhancer of analgesic effect of various analgesics when used in combination, and further found that the dosage and tolerance of the analgesics can be controlled, whereby safe and highly effective analgesic enhancing effect can be achieved. The present invention was accomplished by the above-mentioned findings.

The present invention relates to an analgesic effect enhancing preparation which potentiates the analgesic effect of analgesics, the preparation comprising as an active ingredient an amino acid composition comprising the following amino acids in the following amounts (wt %), more preferably the following suitable amounts (wt %), calculated as free amino acids.

| L-Amino acid | Amount (wt %) | Suitable Amount (wt %) |
|---|---|---|
| leucine | 8.0–16.0 | 10.0–14.0 |
| isoleucine | 4.0–9.0 | 5.0–8.0 |
| valine | 4.0–9.0 | 5.0–8.0 |
| lysine | 6.0–13.0 | 7.0–12.0 |
| threonine | 3.0–6.0 | 3.0–5.0 |
| tryptophan | 1.2–2.0 | 1.2–1.8 |
| methionine | 2.0–5.0 | 3.0–5.0 |
| cysteine | 0.5–2.0 | 0.7–1.0 |
| phenylalanine | 3.0–7.0 | 4.0–7.0 |
| tyrosine | 0.2–1.0 | 0.3–0.5 |
| histidine | 2.0–5.0 | 3.0–5.0 |
| arginine | 30.0–60.0 | 30.0–60.0 |
| alanine | 0.5–2.0 | 1.1–1.7 |
| aminoacetic acid | 0.5–2.0 | 0.8–1.2 |
| serine | 0.2–1.0 | 0.4–0.6 |
| proline | 0.5–2.0 | 0.6–1.0 |
| aspartic acid | 0.1–0.5 | 0.1–0.3 |
| glutamic acid | 0.1–0.5 | 0.1–0.3 |

In the above composition, L-cysteine may partly or wholly be replaced with L-cystine and/or L-methionine, and L-tyrosine may partly or wholly be replaced with phenylalanine, respectively.

The most preferred preparation of the present invention has the following characteristic features: (1) the content of the branched amino acids consisting of L-leucine, L-isoleucine and L-valine are not less than 20 wt % relative to the total amino acids, and (2) the weight ratio of essential amino acids to nonessential amino acids except L-arginine is not less than 30.

The preparation of the present invention can enhance analgesic effect of various kinds of known analgesics. Examples of the analgesics whose analgesic effect can be enhanced by the preparation of the present invention include, for example, narcotic analgesics such as morphine, pethidine hydrochloride, etc.; non-narcotic analgesics such as buprenorphine hydrochloride, pentazocine, tramadol hydrochloride, etc.; antipyretic analgesics such as indomethacin, aspirin, aminopyrine, etc.; antispasmodic analgesics such as atropine, scopolamine, etc.; among which narcotic analgesics or non-narcotic analgesics are preferable. The analgesic effect enhancing preparation of the present invention can exhibit the desired enhancing effect when used in combination with the above-mentioned drugs.

The amino acids used for producing the analgesic effect enhancing preparation of the present invention is preferably crystalline amino acids, and they are employed usually in free forms but not limited thereto. The amino acids may be used in the form of metal salts such as sodium salt, potassium salt, etc., inorganic acid salts such as hydrochloride, sulfate, etc., organic acid salts such as acetate, lactate, malate, etc. Further, the amino acids may be in the form of esters, such as methyl ester, ethyl ester, etc., which can be hydrolysed and converted into free amino acids in vivo. There are cases that the above-mentioned amino acids partly or wholly may be used in the form of N-acyl derivatives such as N-acetyl derivative and the like, as well as in the form of oligopeptides such as dipeptide or the like in which two or more amino acids are linked each other by peptide bonds. When each amino acid is used in the form other than free amino acid form, the amount should be determined so that the calculated amounts of each amino acid as converted into free amino acid fall within the range described above. Among the above-mentioned amino acids used for producing the preparation of the present invention, L-cysteine partly or wholly may be replaced with L-cystine and/or L-methionine, and L-tyrosine partly or wholly may be replaced with phenylalanine, respectively, and the desired analgesic enhancing effect can also be achieved by such replacements.

The analgesic effect enhancing preparation of the present invention may be produced by blending the above-mentioned amounts of amino acids (or the derivative thereof) in the above form, formulating into a preparation suitable for intravenous infusion via peripheral vein, central vein, etc. and is administered to the patients in need of the preparation. Alternatively, a liquid formulation suitable for enteral administration or a powdery formulation which is dissolved when used is also possible.

Similarly to the conventional amino acid preparations, the preparation may contain a suitable pharmaceutical carrier or diluent, and optionally contain a stabilizer, a pH adjusting agent, and other additives. The pH of the preparation is usually adjusted to 3.0–8.0, preferably 4.0–7.0. The concentration of total amino acids in the preparation is similar to those of the conventional amino acid preparations and generally varies from about 8.0 to about 16 w/v %.

The dosage of the preparation according to the present invention may generally range from about 100 to 2000 ml per day, per adult, preferably about 200 to 1000 ml, in the similar manner to those of the conventional amino acid solutions. The dosage may suitably increase or decrease depending on the severity of the disease, nutriture, age, weight etc. of the patients who receive the preparation. The preparation of the present invention is preferably admixed with the conventional various kinds of sugars, fats, electrolytes, vitamins, etc. and is preferably continuously administered via central vein by TPN (Total Parenteral Nutrition).

As a preferable embodiment using the analgesic effect enhancing preparation of the present invention, the preparation is administered to the cancer, postoperative and like patients suffering from pain in combination with the analgesic (combination therapy). The combination therapy using the analgesic is more preferably carried out by administering the analgesic, for example, orally, subcutaneously, intramuscularly, intravenously or rectally while simultaneously infusing the preparation of the present invention.

The amount of the analgesic used in combination with the preparation is suitably determined according to the kind of the analgesic and is not especially limited. The dosage is almost the same as those of the conventionally employed analgesics and is determined to achieve the ordinary levels of analgesic effect. Since the analgesic effect enhancing preparation of the present invention achieves excellent potentiation of analgesic effect, the amount of the analgesic used together with the preparation can remarkably be reduced than conventionally while simultaneously exhibiting sufficiently effective analgesic effect. The decrease in the amount of the analgesic used leads to the reduction of the side effect induced by the analgesic itself. Accordingly, the preparation of the present invention is highly effective.

BEST MODE FOR CARRYING OUT THE INVENTION

Figure 1:
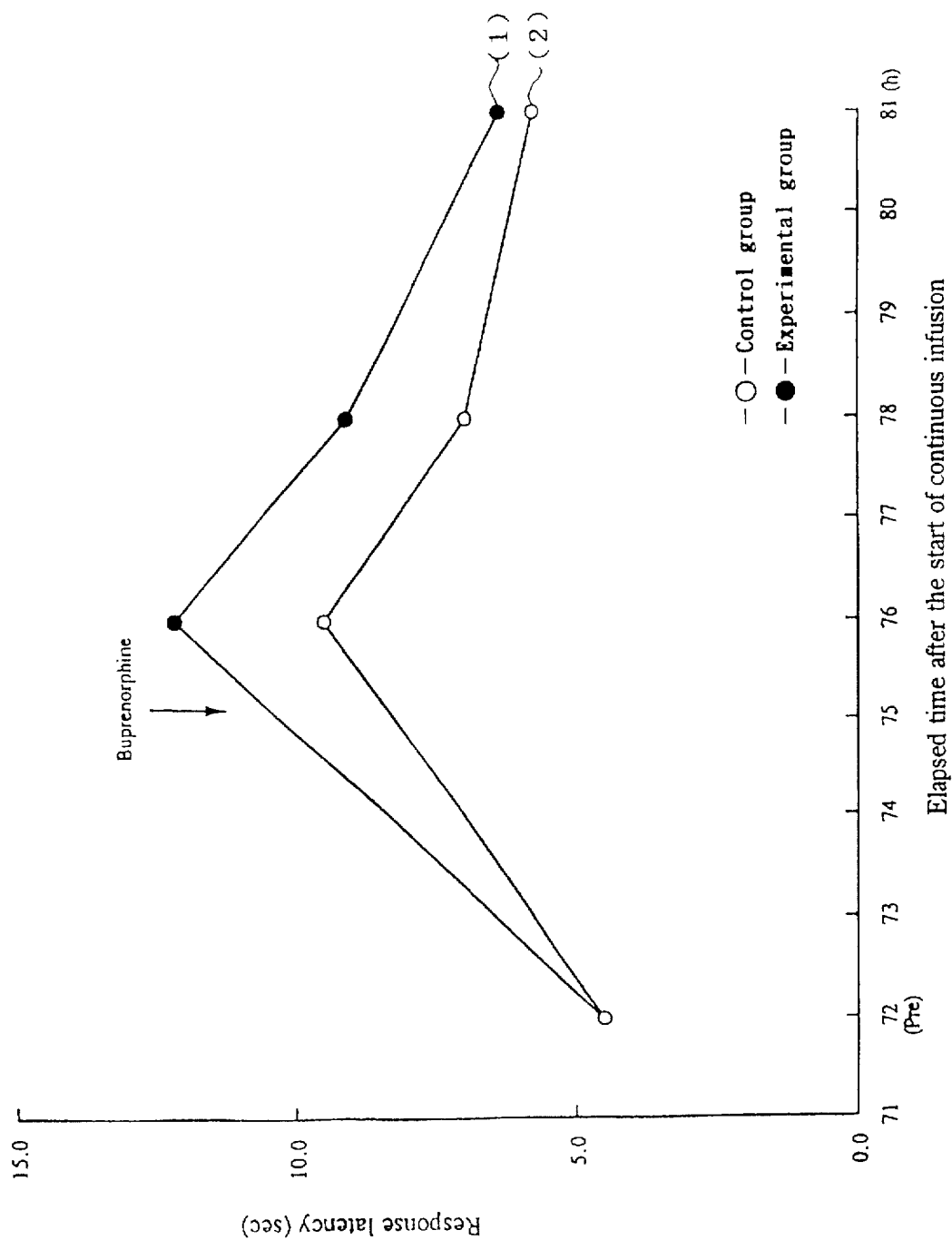
FIG. 1 is a graphical presentation of the test results of analgesic effect (response time latency) evaluated by using Tail-Flick test described in Pharmaceutical Test 1 below.

The present invention is further illustrated by the following Examples which show the process for producing the preparation of the present invention and the test results using the preparation.

EXAMPLE 1

| Amino acid | Amount (g/l) |
| --- | --- |
| L-leucine | 14.00 |
| L-isoleucine | 8.00 |
| L-valine | 8.00 |
| L-lysine | 11.55 |
| L-threonine | 5.15 |
| L-tryptophan | 1.80 |
| L-methionine | 4.30 |
| L-cysteine | 1.00 |
| L-phenylalanine | 6.30 |
| L-tyrosine | 0.50 |
| L-histidine | 4.50 |
| L-arginine | 50.00 |
| L-alanine | 1.65 |
| aminoacetic acid | 1.25 |
| L-serine | 0.60 |
| L-proline | 1.00 |
| L-aspartic acid | 0.20 |
| L-glutamic acid | 0.20 |
| Total free amino acids | 120.00 |

The above-indicated amounts of each amino acid in the form of crystals were added to the distilled water for injection and dissolved therein with stirring. Then to the solution was added a suitable amount of sodium bisulfite as a stabilizer, followed by further addition of the distilled water for injection until the total amount reached 1 l. Then a small amount of acetic acid was added as a pH adjusting agent to achieve the pH of 7.0. The thus prepared amino acid solution was aseptically filtered and poured into a 500 ml glass vial bottle. After replaced with nitrogen, the container was sealed and placed into an autoclave to carry out sterilization at 110° C. for 40 minutes, to thereby give an analgesic effect enhancing preparation of the present invention which was formulated as an amino acid solution for infusion (total amino acids concentration:12.0 w/v %).

EXAMPLE 2

| Amino acid | Amount (g/l) |
| --- | --- |
| L-leucine | 9.60 |
| L-isoleucine | 10.44 |
| L-valine | 10.80 |
| L-lysine | 15.48 |
| L-threonine | 7.20 |
| L-tryptophan | 2.16 |
| L-methionine | 4.32 |
| L-cysteine | 2.16 |
| L-phenylalanine | 8.40 |
| L-tyrosine | 0.60 |
| L-histidine | 5.64 |
| L-arginine | 36.36 |
| L-alanine | 2.04 |
| aminoacetic acid | 2.16 |
| L-serine | 1.08 |
| L-proline | 0.72 |
| L-aspartic acid | 0.48 |
| L-glutamic acid | 0.36 |
| Total free amino acids | 120.00 |

The above-indicated amounts of amino acids were subjected to the same procedures as in Example 1, to give the analgesic effect enhancing preparation of the present invention in the form of an amino acid solution for infusion (total free amino acids concentration:12.0 w/v%).

EXAMPLE 3

| Amino acid | Amount (g/l) |
| --- | --- |
| L-leucine | 10.92 |
| L-isoleucine | 6.60 |
| L-valine | 6.60 |
| L-lysine | 7.20 |
| L-threonine | 3.60 |
| L-tryptophan | 1.20 |
| L-methionine | 2.40 |
| L-cysteine | 0.60 |
| L-phenylalanine | 3.60 |
| L-tyrosine | 0.36 |
| L-histidine | 2.40 |
| L-arginine | 72.00 |
| L-alanine | 0.60 |
| aminoacetic acid | 0.60 |
| L-serine | 0.24 |
| L-proline | 0.84 |
| L-aspartic acid | 0.12 |
| L-glutamic acid | 0.12 |
| Total free amino acids | 120.00 |

The above-indicated amounts of amino acids were subjected to the same procedures as in Example 1, to give the analgesic effect enhancing preparation of the present invention in the form of an amino acid solution for infusion (total free amino acids concentration:12.0 w/v %).

EXAMPLE 4

| Amino acids | Amount (g/l) |
| --- | --- |
| L-leucine | 15.00 |
| L-isoleucine | 12.10 |
| L-valine | 12.10 |
| L-lysine | 16.80 |
| L-threonine | 8.80 |
| L-tryptophan | 3.20 |
| L-methionine | 8.00 |
| L-cysteine | 3.20 |
| L-phenylalanine | 10.40 |
| N-acetyl-L-tyrosine | 1.97 |
| (as L-tyrosine | 1.60) |
| L-histidine | 8.00 |
| L-arginine | 48.00 |
| L-alanine | 3.20 |
| aminoacetic acid | 3.20 |
| L-serine | 1.60 |
| L-proline | 3.20 |
| L-aspartic acid | 0.80 |
| L-glutamic acid | 0.80 |
| Total free amino acids | 160.00 |

The above-indicated amounts of amino acids were subjected to the same procedures as in Example 1, to give the analgesic effect enhancing preparation of the present invention in the form of an amino acid solution for infusion (total free amino acids concentration:16.0 w/v %).

EXAMPLE 5

| Amino acid | Amount (g/l) |
| --- | --- |
| L-leucine | 15.00 |
| L-isoleucine | 13.28 |
| L-valine | 13.98 |
| L-lysine | 12.60 |
| L-threonine | 8.96 |
| L-tryptophan | 2.24 |
| L-methionine | 4.64 |
| L-cysteine | 1.28 |
| L-phenylalanine | 5.30 |
| L-tyrosine | 0.60 |
| L-histidine | 3.40 |
| L-arginine | 72.00 |
| L-alanine | 2.88 |
| aminoacetic acid | 1.92 |
| L-serine | 0.80 |
| L-proline | 0.80 |
| L-aspartic acid | 0.16 |
| L-glutamic acid | 0.16 |
| Total free amino acids | 160.00 |

The above-indicated amounts of amino acids were subjected to the same procedures as in Example 1, to give the analgesic effect enhancing preparation of the present invention in the form of an amino acid solution for infusion (total free amino acids concentration:16.0 w/v %).

EXAMPLE 6

| Amino acid | Amount (g/l) |
| --- | --- |
| L-leucine | 10.85 |
| L-isoleucine | 6.10 |
| L-valine | 6.10 |
| L-lysine | 8.80 |
| L-threonine | 4.10 |
| L-tryptophan | 1.35 |
| L-methionine | 3.35 |
| L-cysteine | 1.35 |
| L-phenylalanine | 4.70 |
| L-tyrosine | 0.60 |
| L-histidine | 3.40 |

-continued

| Amino acid | Amount (g/l) |
| --- | --- |
| L-arginine | 24.00 |
| L-alanine | 1.35 |
| aminoacetic acid | 1.35 |
| L-serine | 0.65 |
| L-proline | 1.35 |
| L-aspartic acid | 0.30 |
| L-glutamic acid | 0.30 |
| Total free amino acids | 80.00 |

The above-indicated amounts of amino acids were subjected to the same procedures as in Example 1, to give the analgesic effect enhancing preparation of the present invention in the form of an amino acid solution for infusion (total free amino acids concentration:8.0 w/v %).

EXAMPLE 7

| Amino acid | Amount (g/l) |
| --- | --- |
| L-leucine | 8.80 |
| L-isoleucine | 5.05 |
| L-valine | 5.05 |
| L-lysine | 7.20 |
| L-threonine | 3.20 |
| L-tryptophan | 1.10 |
| L-methionine | 2.70 |
| L-cysteine | 0.65 |
| L-phenylalanine | 4.00 |
| L-tyrosine | 0.30 |
| L-histidine | 2.85 |
| L-arginine | 36.00 |
| L-alanine | 1.05 |
| aminoacetic acid | 0.70 |
| L-serine | 0.40 |
| L-proline | 0.65 |
| L-aspartic acid | 0.15 |
| L-glutamic acid | 0.15 |
| Total free amino acids | 80.00 |

The above-indicated amounts of amino acids were subjected to the same procedures as in Example 1, to give the analgesic effect enhancing preparation of the present invention in the form of an amino acid solution for infusion (total free amino acids concentration:8.0 w/v %).

EXAMPLE 8

| Amino acid | Amount (g/l) |
| --- | --- |
| L-leucine | 11.65 |
| L-isoleucine | 6.65 |
| L-valine | 6.65 |
| L-lysine | 9.65 |
| L-threonine | 4.30 |
| L-tryptophan | 1.50 |
| L-methionine | 3.60 |
| L-cysteine | 0.85 |
| L-phenylalanine | 5.25 |
| L-tyrosine | 0.40 |
| L-histidine | 3.75 |
| L-arginine | 41.65 |
| L-alanine | 1.40 |
| aminoacetic acid | 1.05 |
| L-serine | 0.50 |
| L-proline | 0.85 |

-continued

| Amino acid | Amount (g/l) |
| --- | --- |
| L-aspartic acid | 0.15 |
| L-glutamic acid | 0.15 |
| Total free amino acids | 100.00 |

The above-indicated amounts of amino acids were subjected to the same procedures as in Example 1, to provide the analgesic effect enhancing preparation of the present invention in the form of an amino acid solution for infusion (total free amino acids concentration:10.0 w/v %).

EXAMPLE 9

| Amino acid | Amount (g/l) |
| --- | --- |
| L-leucine | 14.30 |
| L-isoleucine | 10.30 |
| L-valine | 10.30 |
| L-lysine | 13.50 |
| L-threonine | 6.05 |
| L-tryptophan | 2.10 |
| L-methionine | 5.05 |
| L-cysteine | 1.20 |
| L-phenylalanine | 7.40 |
| L-tyrosine | 0.55 |
| L-histidine | 5.25 |
| L-arginine | 58.30 |
| L-alanine | 1.95 |
| aminoacetic acid | 1.45 |
| L-serine | 0.70 |
| L-proline | 1.20 |
| L-aspartic acid | 0.20 |
| L-glutamic acid | 0.20 |
| Total free amino acids | 140.00 |

The above-indicated amounts of amino acids were subjected to the same procedures as in Example 1, to provide the analgesic effect enhancing preparation of the present invention in the form of an amino acid solution for infusion (total free amino acids concentration:14.0 w/v %).

EXAMPLE 10

| Amino acid | Amount (g/l) |
| --- | --- |
| L-leucine | 14.00 |
| L-isoleucine | 8.00 |
| L-valine | 8.00 |
| L-lysine hydrochloride | 14.43 |
| (as L-lysine | 11.55) |
| L-threonine | 5.15 |
| L-tryptophan | 1.80 |
| L-methionine | 4.30 |
| L-cysteine | 1.00 |
| L-phenylalanine | 6.30 |
| L-tyrosine | 0.50 |
| L-histidine | 4.50 |
| L-arginine | 50.00 |
| L-alanine | 1.65 |
| aminoacetic acid | 1.25 |
| L-serine | 0.60 |
| L-proline | 1.00 |
| L-aspartic acid | 0.20 |
| L-glutamic acid | 0.20 |
| Total free amino acids | 120.00 |

The above-indicated amounts of amino acids were subjected to the same procedures as in Example 1, to give the analgesic effect enhancing preparation of the present invention in the form of an amino acid solution for infusion (total free amino acids concentration:12.0 w/v %).

EXAMPLE 11

| Amino acid | Amount (g/l) |
| --- | --- |
| L-leucine | 14.00 |
| L-isoleucine | 8.00 |
| L-valine | 8.00 |
| L-lysine malate | 22.14 |
| (as L-lysine | 11.55) |
| L-threonine | 5.15 |
| L-tryptophan | 1.80 |
| L-methionine | 4.30 |
| L-cysteine | 1.00 |
| L-phenylalanine | 6.30 |
| L-tyrosine | 0.50 |
| L-histidine | 4.50 |
| L-arginine | 50.00 |
| L-alanine | 1.65 |
| aminoacetic acid | 1.25 |
| L-serine | 0.60 |
| L-proline | 1.00 |
| L-aspartic acid | 0.20 |
| L-glutamic acid | 0.20 |
| Total free amino acids | 120.00 |

The above-indicated amounts of amino acids were subjected to the same procedures as in Example 1, to give the analgesic effect enhancing preparation of the present invention in the form of an amino acid solution for infusion (total free amino acids concentration:12.0 w/v %).

EXAMPLE 12

| Amino acid | Amount (g/l) |
| --- | --- |
| L-leucine | 14.00 |
| L-isoleucine | 8.00 |
| L-valine | 8.00 |
| L-lysine | 11.55 |
| L-threonine | 5.15 |
| N-acetyl-L-tryptophan | 2.17 |
| (as L-tryptophan | 1.80) |
| L-methionine | 4.30 |
| L-cysteine | 1.00 |
| L-phenylalanine | 6.30 |
| L-tyrosine | 0.50 |
| L-histidine | 4.50 |
| L-arginine | 50.00 |
| L-alanine | 1.65 |
| aminoacetic acid | 1.25 |
| L-serine | 0.60 |
| L-proline | 1.00 |
| L-aspartic acid | 0.20 |
| L-glutamic acid | 0.20 |
| Total free amino acids | 120.00 |

The above-indicated amounts of amino acids were subjected to the same procedures as in Example 1, to give the analgesic effect enhancing preparation of the present invention in the form of an amino acid solution for infusion (total free amino acids concentration:12.0 w/v %).

EXAMPLE 13

| Amino acid | Amount (g/l) |
| --- | --- |
| L-leucine | 14.00 |
| L-isoleucine | 8.00 |
| L-valine | 8.00 |
| L-lysine | 11.55 |
| L-threonine | 5.15 |
| L-tryptophan | 1.80 |
| L-methionine | 4.30 |
| L-cysteine | 1.00 |
| L-phenylalanine | 6.30 |
| L-tyrosine | 0.50 |
| L-histidine | 4.50 |
| L-arginine monohydrochloride | 60.47 |
| (as arginine | 50.00) |
| L-alanine | 1.65 |
| aminoacetic acid | 1.25 |
| L-serine | 0.60 |
| L-proline | 1.00 |
| L-aspartic acid | 0.20 |
| L-glutamic acid | 0.20 |
| Total free amino acids | 120.00 |

The above-indicated amounts of amino acids were subjected to the same procedures as in Example 1, to give the analgesic effect enhancing preparation of the present invention in the form of an amino acid solution for infusion (total free amino acids concentration:12.0 w/v %).

EXAMPLE 14

| Amino acid | Amount (g/l) |
| --- | --- |
| L-leucine | 14.00 |
| L-isoleucine | 8.00 |
| L-valine | 8.00 |
| L-lysine | 11.55 |
| L-threonine | 5.15 |
| L-tryptophan | 1.80 |
| L-methionine | 4.30 |
| L-cysteine | 1.00 |
| L-phenylalanine | 6.30 |
| L-tyrosine | 0.50 |
| L-histidine hydrochloride hydrate | 6.08 |
| (as L-histidine | 4.50) |
| L-arginine | 50.00 |
| L-alanine | 1.65 |
| aminoacetic acid | 1.25 |
| L-serine | 0.60 |
| L-proline | 1.00 |
| L-aspartic acid | 0.20 |
| L-glutamic acid | 0.20 |
| Total free amino acids | 120.00 |

The above-indicated amounts of amino acids were subjected to the same procedures as in Example 1, to give the analgesic effect enhancing preparation of the present invention in the form of an amino acid solution for infusion (total free amino acids concentration:12.0 w/v %).

Pharmacological Test 1

While performing continuous infusion of the analgesic effect enhancing preparation (amino acid solution) of the present invention prepared by Example 1, buprenorphine was administered and analgesic effect enhancing ability (combination effect) of the preparation of the present invention was evaluated by employing the following procedures.

1. Experimental Solution, Control Solution and the Combination Substance

A 200 ml quantity of "GE-2" (product of Otsuka Pharmaceutical Co., Ltd., a total electrolytes solution, whose composition and nature are indicated in Table 2) and 1 ml of "Otsuka MV injection" (product of Otsuka Pharmaceutical Co., Ltd., a multivitamin injection) were added to 100 ml of the analgesic effect enhancing preparation of the present invention (formulated as an infusion solution) having the composition and the nature indicated in Table 1 and 106 ml of a commercially available amino acid solution (control) having the composition and the nature indicated in Table 1, respectively, to provide an experimental solution and a control solution.

TABLE 1

| Amino acids | analgesic effect enhancing preparation of the present invention Example 1 (w/v %) | commercially available injection "Proteamine 12" (w/v %) |
|---|---|---|
| L-leucine | 1.400 | 1.138 |
| L-isoleucine | 0.800 | 0.597 |
| L-valine | 0.800 | 0.690 |
| L-methionine | 0.430 | 0.433 |
| L-phenylalanine | 0.630 | 0.974 |
| L-tryptophan | 0.180 | 0.187 |
| L-threonine | 0.515 | 0.504 |
| acetic acid · L-lysine | 1.629 | — |
| acetic acid · L-lysine | — | 0.980 |
| (as L-lysine | 1.155 | 0.784) |
| aminoacetic acid | 0.125 | 1.568 |
| L-alanine | 0.165 | 0.821 |
| L-serine | 0.060 | 0.467 |
| L-aspartic acid | 0.020 | 0.202 |
| L-glutamic acid | 0.020 | 0.102 |
| L-histidine | 0.450 | (0.523) |
| L-histidine hydrochloride | — | 0.706 |
| L-tyrosine | 0.050 | 0.057 |
| L-proline | 0.100 | 1.063 |
| L-cysteine | 0.100 | 0.023 |
| L-arginine | 5.000 | (1.230) |
| L-arginine hydrochloride | — | 1.488 |
| total free amino acids | 12.000 | 11.362 |
| essential amino acids (E) | 5.910 | 5.307 |
| nonessential amino acids (N) | 6.090 | 6.056 |
| E/N ratio | 0.970 | 0.876 |
| branched amino acids (%) | 25.00 | 21.34 |
| total nitrogen content (mg/ml) | 25.50 | 18.15 |
| $Na^+$ (mEq/l) | 1.92 | 150 |
| $Cl^-$ (mEq/l) | — | 150 |
| Acetate (mEq/l) | 221.0 | — |
| Lactate (mEq/l) | 143.0 | — |
| pH | about 7.0 | 5.7–6.7 |
| osmotic pressure ratio* | about 4.2 | about 5 |

TABLE 2

| ingredient (w/v %) | GE-2 |
|---|---|
| glucose | 29.2 |
| dipotassium hydrogenphosphate | 0.261 |
| sodium chloride | 0.283 |
| potassium acetate | 0.115 |
| calcium chloride | 0.073 |
| magnesium sulfate | 0.123 |
| sodium citrate | 0.097 |
| zinc sulfate | 9.6 (ppm) |
| citric acid | 0.165 |
| electrolytes composition | |
| $Na^+$ | 35 |
| $K^+$ | 25 |
| $Mg^{2+}$ | 6 |
| $Ca^{2+}$ | 6 |

TABLE 2-continued

| ingredient (w/v %) | GE-2 |
|---|---|
| $Cl^-$ | 35 |
| $SO_4^{2-}$ | 6 |
| Acetate$^-$ | 7 |
| Citrate$^{3-}$ | 20 |
| P (mmol/600 ml) | 10 |
| Zn (μmol/600 ml) | 20 |
| pH | 4.9 |
| titratable acidity | 21.0 |
| osmotic pressure ratio* | about 6 | osmotic pressure ratio * is the ratio to the physiological saline

"Lepetan injection" (product of Otsuka Pharmaceutical Co., Ltd.) containing 0.2 mg of buprenorphine in 1 ml thereof was used to administer buprenorphine hydrochloride (combination substance) as a test analgesic. Lepetan injection was diluted with a physiological saline when used to provide a concentration of buprenorphine of 0.01 mg/ml or 0.02 mg/ml and then administered subcutaneously using a syringe in order to give a dosage of 2 ml/kg.

2. Animals and Breeding Conditions

Forty male Wistar rats, Slc, 7 weeks of age were purchased, divided into the groups each consisting of five rats and housed respectively in polycarbonate cages. The rats were bred and conditioned for the period of eight days under temperature of 24±2° C., humidity of 55±10%, a 12 hr light cycle (lights on from 7 a.m. to 7 p.m.) and ventilation of 13 times per hour. During the conditioning, the rats were allowed to freely access solid feed (MF, Oliental Yeast Industry Co., Ltd.) and water.

Then, the rats were individually housed in the metabolic cage to receive continuous infusion of the test solution and subjected to the following test. During the test, the rats were not supplied with feed and water.

3. Experimental Group Constitution and Grouping

Four groups each consisting of eight rats were established; two groups which receive the control solution were injected with 0.02 ml/kg and 0.04 mg/kg of buprenorphine, respectively, and the remaining two groups which receive the experimental solution were injected with 0.02 mg/kg and 0.04 mg/kg of buprenorphine, respectively. The test animals were selected in order that the results of the Randall-Selitto pain threshold test using right and left hindpaws measured at day 1 of the test did not vary, and were grouped by the stratified continuously randomized method referring to the values of pain threshold.

4. Administration Regimen and Dosage of the Infusion Solution

The rats were cannulated into the superior vena cava with a catheter and infused with the test solution for a period of three days.

The dosage of each test solution was determined to give 300 ml/kg/day based on the body weight measured immediately after implanting the catheter. Since the day of the catheter implantation corresponded to a sugar administering day, the amount of solution dosed was reduced by half.

5. Control of the Infusion Solution

After Otsuka MV injection was admixed with each test solution, the scale mark of the syringe and the onset time were recorded. The amount of the solution dosed in a day was calculated by subtracting the remaining amount in the syringe measured at 9:00 a.m. in the next morning from the set amount and by referring to the dosing duration, then the pumping scale was re-adjusted so as to give the dosage of 300 ml/kg/day.

6. Preparation of the Brewer's Yeast Solution and the Administration Thereof A 10% brewer's yeast suspension was prepared by suspending Brewer's yeast (Sigma Chemical) in a physiological saline, and each rat was injected with 0.1 ml of the suspension subcutaneously by a syringe in the right footpad.

7. Test Procedures

7.1. Assessment of Analgesic Effect by the Tail-Flick Test

According to the D'Amour-Smith method (European Journal of Pharmacology, 236, 137 (1993)), the radiant heat tail-flick test was performed and the latencies of the tail-flick response time were measured using the Tail-Flick analgesic effect measuring device. The latency of the tail-flick response time was measured before implanting the catheter and 72 hr after the start of continuous infusion and analgesic effects were compared between the control solution and the experimental solution.

Next, 73 hr after the start of continuous infusion of each solution, the rats were injected with the brewer's yeast suspension in the right footpad, and two hours after the brewer's yeast injection, the combination substance (buprenorephine) was injected subcutaneously. Then, 1, 3 and 6 hours after the buprenorphine injection, the latencies of tail-flick response time were measured and enhancement of analgesic effect was assessed and compared between the combination of buprenorphine plus the control solution and the combination of buprenorphine plus the experimental solution.

7.2. Assessment of Analgesic Effect by the Randall-Selitto Test

According to the Randall-Selitto test (European Journal of Pharmacology, 218, 153 (1992)), the pressure required to elicit a struggle response in each rat was determined by applying pressure to both right and left hindpaws using the Randall-Selitto analgesic effect measuring device. Pain thresholds in the right and left intact paws were measured before implanting the catheter and 72 hours after the start of continuous infusion, and analgesic effects were compared between the control solution and the experimental solution.

Next, 73 hours after the start of continuous infusion, the rats were injected with the brewer's yeast suspension subcutaneously in the right footpad, and two hours after the brewer's yeast injection, the combination substance (buprenorphine) was injected subcutaneously. Then, 1, 3 and 6 hours after the buprenorphine injection, pain thresholds were measured in the inflamated and intact paws to assess enhancement of analgesic effect of buprenorphine by simultaneously administering the control solution and the experimental solution, respectively.

8. Statistical Analysis

Test data obtained were presented as means±SE and were analyzed by Student's test. The control solution and the experimental solution were respectively evaluated for their analgesic effect before implanting the catheter and 72 hours after the start of continuous infusion, and the results were also compared between the two groups. Enhancement of analgesic effect by simultaneously administering the control solution and the experimental solution, respectively, was checked at 72 hr after continuous infusion and at 1, 3 and 6 hr after the buprenorphine injection. The results obtained at every measuring point were also compared between the control groups and the experimental groups.

9. Test Results

(1) Body Weights

Changes in the rats body weights were checked with the time-course of the test, and the rats weights of the experimental groups were almost similar to those of the control groups through the observation period.

(2) Assessment of Analgesic Effect by the Tail-Flick Test

The results were shown in FIG. 1. In the graph, elapsed time after the start of continuous infusion (hour) was indicated along the abscissa and the response latency (second) was indicated along the ordinate. The line (1) indicates the results of the experimental groups receiving the preparation of the present invention and the line (2) indicates the results obtained by the control groups. In the graph, the arrow demonstrates the time of administering the brewery's yeast solution and buprenorphine, respectively.

As indicated by the results, the start of continuous infusion did not produce any change in the response latencies both in the control groups and in the experimental groups, and even at 72 hr after continuous infusion, no notable difference was observed between the control groups and the experimental groups.

By applying subcutaneous injection of buprenorphine at 75 hr after continuous infusion, the response latency was prolonged in the control groups receiving 0.04 mg/kg of buprenorphine, whereas in the experimental groups receiving 0.04 mg/kg of buprenorphine a significant prolongation of response latency was observed in the dose dependent manner and the latency values of the experimental groups were higher than those of the control groups.

3. Assessment of Analgesic Effect by the Randall-Selitto Test

Figure 3:
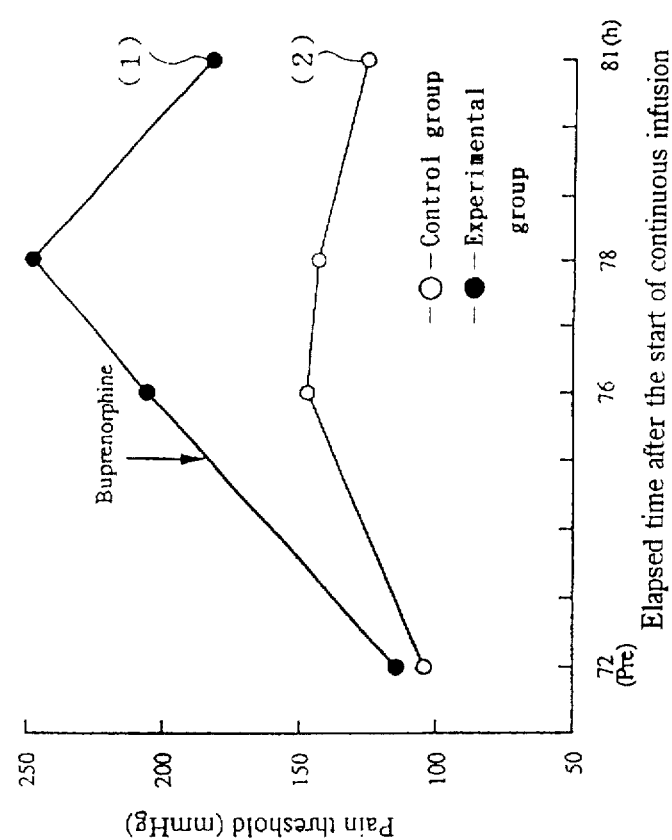
FIG. 3 is a graphical presentation of the test results applied on the intact paws (pain threshold) evaluated by using Randall-Selitto test described in Pharmaceutical Test 1 below.
Figure 2:
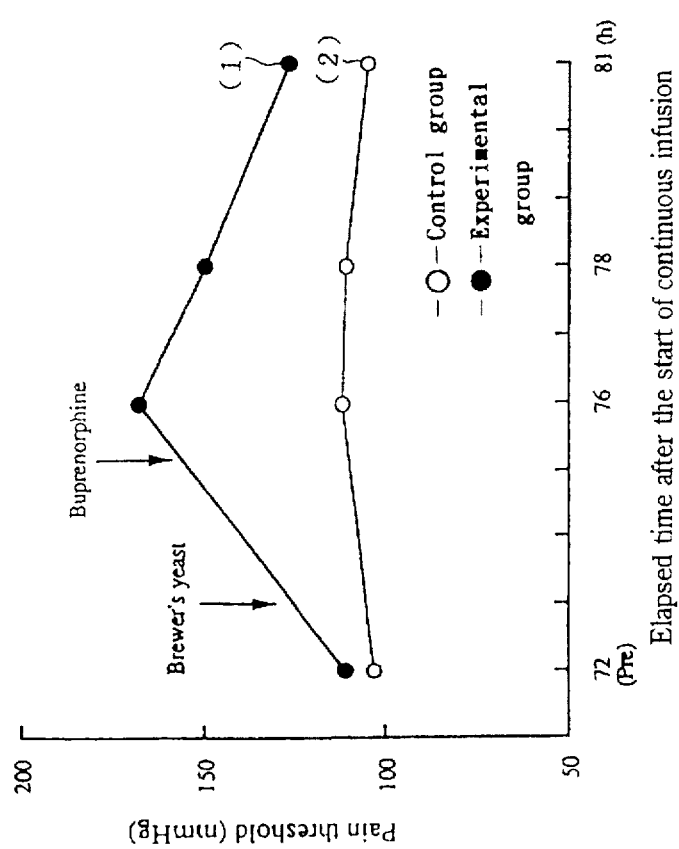
FIG. 2 is a graphical presentation of the test results applied on the inflamed paws (pain threshold) evaluated by using Randall-Selitto test described in Pharmaceutical Test 1 below.

The results are shown in FIG. 2 (inflamed right paw) and in FIG. 3 (intact left paw).

In each FIG., elapsed time after the start of continuous infusion (hour) was indicated along the abscissa and pain threshold (mmHg) was indicated along the ordinate. The line (1) indicates the results of the experimental groups receiving preparation of the present invention and the line (2) indicates the results obtained by the control groups. In the graphs, arrows demonstrate the time of administering the brewery's yeast solution and buprenorphine, respectively.

As is apparent from the results presented in the FIGs, there is no change in the pain thresholds in the control groups even by injecting 0.04 mg/kg of buprenorphine in both right and left intact paws at 72 hr after continuous infusion, as compared to the results measured before the start of the control solution infusion. By contrast, a significant increase or increasing tendency was observed in the pain thresholds in the experimental groups and the pain threshold values were higher than those of the control groups.

In the control groups receiving 0.04 mg/kg of buprenorphine at 75 hr after continuous infusion, a significant increase in the response latency was observed only in the intact paws, as compared to the condition before administering buprenorphine. In the experimental groups, a significant increase or increasing tendency in the pain threshold was observed by administering 0.04 mg/kg of buprenorphine both in the intact and inflamed paws, and a significant increase or increasing tendency in the pain threshold was observed in the intact paws, and the degree of the increase was higher than that of the control groups.

In view of the above results, the analgesic effect enhancing preparation of the present invention can achieve significant enhancement of analgesic effect of the analgesic.

Industrial Applicability

The analgesic effect enhancing preparation of the present invention can potentiate analgesic effect of various kinds of analgesics which are administered in combination therewith. The preparation can safely and effectively be applied to the seriously invaded patients such as cancer patients, postoperative patients and the like who suffer from various pains.

We claim:

1. A method for enhancing analgesia in a cancer patient by administering to the patient an analgesic and a pharmaceutically effective amount of an analgesic effect enhancing preparation, the preparation comprising the following amino acids in the following proportions, calculated as free amino acids:

| L-Amino acid | Proportion (wt %) |
| --- | --- |
| leucine | 8.0–16.0 |
| isoleucine | 4.0–9.0 |
| valine | 4.0–9.0 |
| lysine | 6.0–13.0 |
| threonine | 3.0–6.0 |
| tryptophan | 1.2–2.0 |
| methionine | 2.0–5.0 |
| cysteine | 0.5–2.0 |
| phenylalanine | 3.0–7.0 |
| tyrosine | 0.2–1.0 |
| histidine | 2.0–5.0 |
| arginine | 30.0–60.0 |
| alanine | 0.5–2.0 |
| aminoacetic acid | 0.5–2.0 |
| serine | 0.2–1.0 |
| proline | 0.5–2.0 |
| aspartic acid | 0.1–0.5 |
| glutamic acid | 0.1–0.5 | wherein the cysteine is present or is partly or wholly replaced with cystine and/or methionine and the tyrosine is present or is partly or wholly replaced with phenylalamine.

2. A method as claimed in claim 1, wherein the cysteine is not replaced with cystine or methionine and the tyrosine is not replaced with phenylalanine.

3. A method as claimed in claim 1, wherein the preparation comprises the following amino acids in the following proportions, calculated as free amino acids:

| L-Amino acid | Proportion (wt %) |
| --- | --- |
| leucine | 10.0–14.0 |
| isoleucine | 5.0–8.0 |
| valine | 5.0–8.0 |
| lysine | 7.0–12.0 |
| threonine | 3.0–5.0 |
| tryptophan | 1.2–1.8 |
| methionine | 3.0–5.0 |
| cysteine | 0.7–1.0 |
| phenylalanine | 4.0–7.0 |
| tyrosine | 0.3–0.5 |
| histidine | 3.0–5.0 |
| arginine | 30.0–60.0 |
| alanine | 1.1–1.7 |
| aminoacetic acid | 0.8–1.2 |
| serine | 0.4–0.6 |
| proline | 0.6–1.0 |
| aspartic acid | 0.1–0.3 |
| glutamic acid | 0.1–0.3 | wherein the cysteine is present or is partly or wholly replaced with cystine and/or methionine and the tyrosine is present or is partly or wholly replaced with phenylalamine.

4. A method as claimed in claim 3, wherein the cysteine is not replaced with cystine or methionine and the tyrosine is not replaced with phenylalanine.

5. A method for enhancing analgesia in a postoperative patient by administering to the patient an analgesic and a pharmaceutically effective amount of an analgesic effect enhancing preparation, the preparation comprising the following amino acids in the following proportions, calculated as free amino acids:

| L-Amino acid | Proportion (wt %) |
| --- | --- |
| leucine | 8.0–16.0 |
| isoleucine | 4.0–9.0 |
| valine | 4.0–9.0 |
| lysine | 6.0–13.0 |
| threonine | 3.0–6.0 |
| tryptophan | 1.2–2.0 |
| methionine | 2.0–5.0 |
| cysteine | 0.5–2.0 |
| phenylalanine | 3.0–7.0 |
| tyrosine | 0.2–1.0 |
| histidine | 2.0–5.0 |
| arginine | 30.0–60.0 |
| alanine | 0.5–2.0 |
| aminoacetic acid | 0.5–2.0 |
| serine | 0.2–1.0 |
| proline | 0.5–2.0 |
| aspartic acid | 0.1–0.5 |
| glutamic acid | 0.1–0.5 | wherein the cysteine is present or is partly or wholly replaced with cystine and/or methionine and the tyrosine is present or is partly or wholly replaced with phenylalamine.

6. A method as claimed in claim 5, wherein the cysteine is not replaced with cystine or methionine and the tyrosine is not replaced with phenylalanine.

7. A method as claimed in claim 5, wherein preparation comprises the following amino acids in the following preparations, calculated as free amino acids:

| L-Amino acid | Proportion (wt %) |
| --- | --- |
| leucine | 10.0–14.0 |
| isoleucine | 5.0–8.0 |
| valine | 5.0–8.0 |
| lysine | 7.0–12.0 |
| threonine | 3.0–5.0 |
| tryptophan | 1.2–1.8 |
| methionine | 3.0–5.0 |
| cysteine | 0.7–1.0 |
| phenylalanine | 4.0–7.0 |
| tyrosine | 0.3–0.5 |
| histidine | 3.0–5.0 |
| arginine | 30.0–60.0 |
| alanine | 1.1–1.7 |
| aminoacetic acid | 0.8–1.2 |
| serine | 0.4–0.6 |
| proline | 0.6–1.0 |
| aspartic acid | 0.1–0.3 |
| glutamic acid | 0.1–0.3 | wherein the cysteine is present or is partly or wholly replaced with cystine and/or methionine and the tyrosine is present or is partly or wholly replaced with phenylalamine.

8. A method as claimed in claim 7, wherein the cysteine is not replaced with cystine or methionine and the tyrosine is not replaced with phenylalanine.

* * * * *